United States Patent [19]

Olsen et al.

[11] Patent Number: 4,688,998
[45] Date of Patent: Aug. 25, 1987

[54] MAGNETICALLY SUSPENDED AND ROTATED IMPELLOR PUMP APPARATUS AND METHOD

[76] Inventors: Don B. Olsen, 8832 Blue Jay La., Salt Lake City, Utah 84121; Günter Bramm, Luisen Str. 49, 8000 Munich 2; Pavel Novak, Görres Str. 2, D-8000-Munich 40, both of Fed. Rep. of Germany

[21] Appl. No.: 926,872

[22] Filed: Nov. 4, 1986

Related U.S. Application Data

[63] Continuation of Ser. No. 732,884, May 8, 1985, abandoned, which is a continuation of Ser. No. 245,007, Mar. 18, 1981, abandoned.

[51] Int. Cl.⁴ .............................................. F04B 17/00
[52] U.S. Cl. .............................. 417/356; 415/DIG. 4; 128/1 D; 623/3
[58] Field of Search ............... 417/353, 354, 355, 356, 417/316; 415/DIG. 4, 206, 215; 604/4, 131, 151; 623/3; 128/1 D, DIG. 3

[56] References Cited

U.S. PATENT DOCUMENTS

| | | |
|---|---|---|
| Re. 27,849 | 12/1973 | Wortman . |
| 1,105,967 | 8/1914 | Davidson ........................ 415/206 X |
| 1,711,045 | 4/1929 | Davis ................................ 417/356 |
| 2,263,515 | 11/1941 | Pezzillo ............................. 417/356 |
| 2,319,730 | 5/1943 | Garraway ......................... 417/356 |
| 2,500,400 | 3/1950 | Cogswell .......................... 417/356 |
| 3,194,165 | 7/1965 | Sorlin ................................ 417/356 |
| 3,433,163 | 3/1969 | Sheets et al. ..................... 417/353 |
| 3,647,324 | 3/1972 | Rafferty et al. .................. 417/420 |
| 3,938,913 | 2/1976 | Isenberg et al. .................. 417/356 |
| 3,957,389 | 5/1976 | Rafferty et al. ............. 415/DIG. 4 |
| 3,970,408 | 7/1976 | Rafferty et al. ............. 415/DIG. 4 |
| 4,213,207 | 7/1980 | Wilson ........................... 128/1 D X |

FOREIGN PATENT DOCUMENTS

| | | |
|---|---|---|
| 1202392 | 10/1965 | Fed. Rep. of Germany . |
| 2341766 | 2/1975 | Fed. Rep. of Germany . |
| 2420825 | 11/1975 | Fed. Rep. of Germany . |
| 2457783 | 6/1976 | Fed. Rep. of Germany . |
| 2515608 | 9/1976 | Fed. Rep. of Germany . |
| 2177339 | 11/1973 | France . |
| 361209 | 7/1938 | Italy .................................... 415/215 |

OTHER PUBLICATIONS

D. M. Lederman, R. D. Cumming, H. E. Petschek, T.-H. Chiu, E. Nyilas, and E. W. Salzman, "An Instrumental Approach to In Vivo Hemocompatibility Assessment: Development of the Intravascular Magnetic Suspension of a Test Device," *Annals of the New York Academy of Sciences*, vol. 283, pp. 524–535, Feb. 10, 1977.

*Primary Examiner*—Leonard E. Smith
*Attorney, Agent, or Firm*—Dunlap, Codding & Peterson

[57] ABSTRACT

A novel pump apparatus and method, the pump including a magnetically suspended and rotated impellor inside the pump housing. A novel sensor system detects the position of the impellor and thus provides the necessary information for operation of a suspension circuit for magnetically suspending the impellor. A valve member may be included as part of the impellor to prevent reverse flow in the event of impellor failure when used as a ventricular assist device.

3 Claims, 13 Drawing Figures

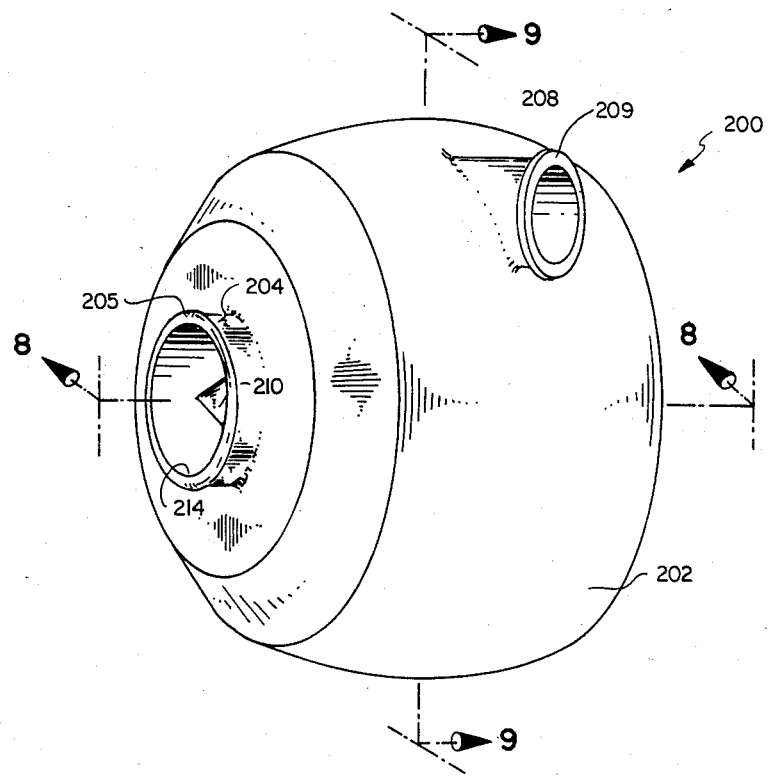
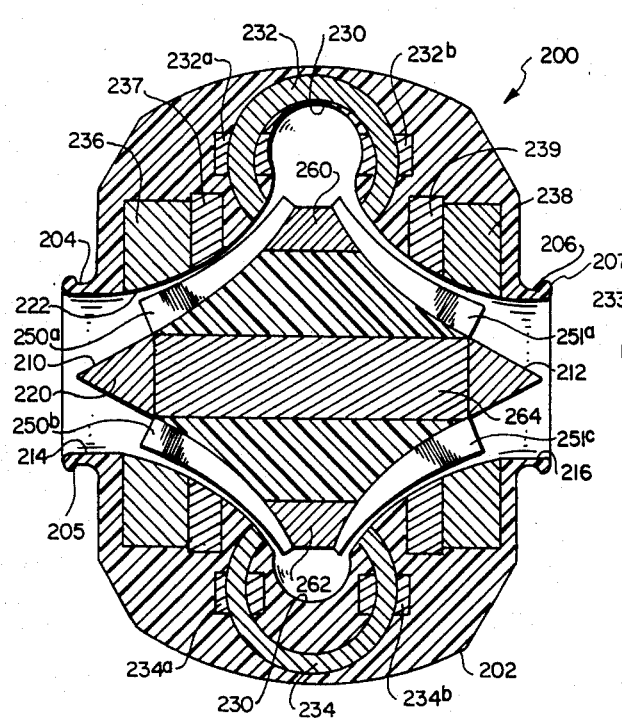
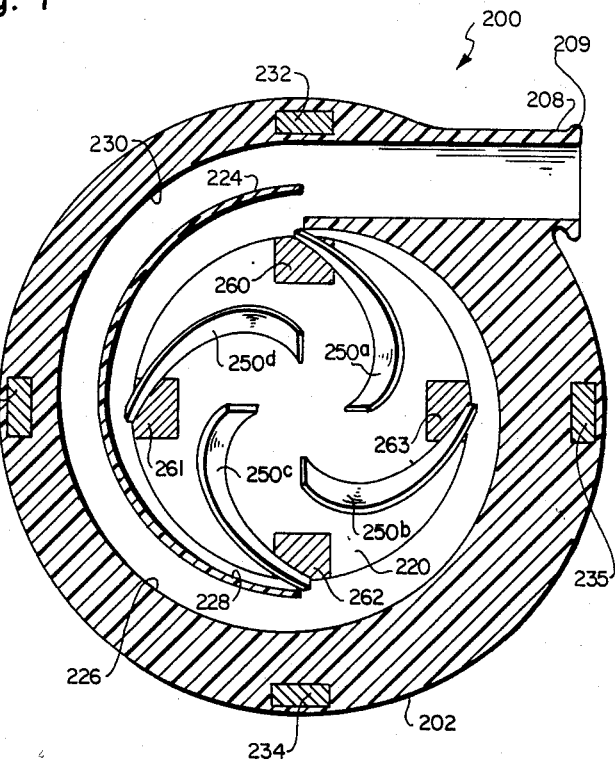
Fig. 7
Fig. 8
Fig. 9

MAGNETICALLY SUSPENDED AND ROTATED IMPELLOR PUMP APPARATUS AND METHOD

This application is a continuation of Ser. No. 732,884, filed May 8, 1985, now abandoned, which is a continuation of Ser. No. 245,007, filed Mar. 18, 1981, now abandoned.

BACKGROUND

1. Field of the Invention

This invention relates to pumps and, more particularly, to a novel pump apparatus and method, the pump including a magnetically suspended and rotated impellor.

2. The Prior Art.

Historically, fluids are pumped by a variety of pump apparatus including, for example, positive displacement pumps such as piston-type pumps, moving diaphragm pumps, peristaltic action pumps, and the like. The conventional centrifugal-type pump involves a shaft-mounted impellor immersed in the fluid. The shaft extends through a seal and bearing apparatus to a drive mechanism. However, it is well-documented that shaft seals are notoriously susceptible to wear and also attack by the fluids, resulting in an ultimate leakage problem.

It is also well known that certain special applications require specific pumping techniques. For example, fluids such as corrosive fluids (acids or caustics) and sensitive fluids such as blood, each require specialized pumping techniques.

The pumping of blood involves known hazards. In particular, the shaft seal for an impellor-type blood pump is an area of stagnation and excessive heat. These events foster the formation of thrombus and provide a place for bacterial growth. Seal leakage can also lead to bearing freezing. Numerous attempts to avoid the foregoing problems associated with pumping blood have been made using flexible diaphragm and collapsible tubing in roller pumps. However, the continual flexing of the diaphragm and/or the tubing material is known to (1) change the blood-contacting properties of the material, (2) result in material fatigue with the attendant risk of an eventual rupture, and (3) dislodge fragments of the internal wall of the flexible material causing the fragments to pass as emboli into the bloodstream.

Studies have been made of pumps used as total artificial hearts implanted in experimental animals. These studies have continued for the past 20 years. These pumps can be categorized as producing pulsatile or nonpulsatile flows. Pulsatile pumps universally require valves (mechanical or tissue) with their inherent problems and limitations. While the nonpulsatile pumps generally do not require valve systems, they do require rotating shafts passing through bearings and seals with the inherent problems set forth hereinbefore. Most of these systems (non-pulsatile) have been implanted outside of the body for short-term cardiac assistance and have experienced a moderate degree of success.

Historically, the pump mechanism of these total artificial hearts have been energized with gases (pneumatic systems), electricity (motors, solenoids, etc.), nuckkar energy, and skeletal muscles. The energy sources and their convertor systems possess additional components that increase the complexity of the total systems and thereby contribute to the overall unreliability of the systems. Also, the energy conversion system must be correlated and integrated into the pump design and the total design must be configured to fit within the available anatomical space. Other drawbacks include (1) high-bulk characteristics, (2) dependence on external pneumatic systems, (3) choice of available materials for fabrication, and (4) multiple bearings and moving parts with inherent limitations in the tested and predicted life expectancies of the same. Most prior art systems inherently have excessively high (1) noise characteristics, (2) vibration, and (3) recoil (thrust) levels.

The current state of the art for blood pumps is being developed in at least four laboratories in the United States. Survival times for calves with total artificial heart replacements of about five months have been experimentally achieved with the longest living about seven months. The natural ventricles of a man have been replaced at least once by a total artificial heart in one reported incident as early as 1969.

One of the inventors has been closely associated with animal experiments involving both total artificial hearts and ventricular assist devices for at least seven years. As a result, he has held most of the survival records obtained with calves having the total artificial heart. These records include at least 38 days for an electromechanical system and 221 days for a pneumatic system. Accordingly, this inventor is very familiar with current research in total artificial hearts and assist devices throughout the world and is thus congnizant of the many problems and limitations with the current state of the art blood pumps. For example, U.S. Pat. No. 3,641,591 involves a flexing diaphragm that limits the material selection and requires a portable energy supply. U.S. Pat. Nos. 3,633,217 and 3,733,616 are electromagnetically activated and involve flexing diaphragms, mechanical linkages, with a corresponding increased weight and bulk. U.S. Pat. No. 3,896,501 is an electromechanical device having a complexity of gears, shafts, and bearings with the attendant problems set forth hereinbefore. Electro-hydraulic systems include U.S. Pat. Nos. 3,048,165; 3,148,624; 3,572,979; 3,636,570; and 3,783,453 and variously involve flexing diaphragms, springs, hydraulic fluid containment tubing and valving in addition to increased bulk and weight.

All of the above, non-pneumatic, blood pumps require a compliance chamber when used in a singular or biventricular assist mode or as a total artificial heart. This compliance chamber must accommodate a volume equal to each stroke volume in the assist device and aid in balancing the differences in right and left ventricular stroke volumes.

U.S. Pat. Nos. 1,061,142; 2,669,668; 3,139,832; 3,411,450; 3,420,184; 3,487,784; 3,608,088; and 3,647,324 all involve electrically powered centrifugal pumps. These pumps each include a rotating shaft, the shaft passing through a seal in the pumping chamber directly from a motor or a magnetic coupler. As set forth hereinbefore, any seal usually constitutes a very hazardous environment while also being subject to failure by leakage into the shaft bearings.

It would, therefore, be a significant advancement in the art to provide a pump characterized by the absence of rotating shafts, seals, bearings, or the like. It would also be an advancement in the art to provide a novel pump apparatus and method whereby the impellor for the pump is magnetically suspended and rotated in the fluid being pumped. It would also be an advancement in the art to provide a novel method for pumping a fluid with a magnetically suspended pump impellor. Another advancement in the art is to provide a novel pump apparatus that is characterized by the absence of valves in the stream flow. It would also be an advancement in the art to provide a pump having a novel valve apparatus in combination with the impellor so that when power is interrupted to the impellor, the valving action automatically closes under reverse flow when the pump is used in the ventricular assist mode. Such a novel pump apparatus and method is disclosed and claimed herein.

BRIEF SUMMARY AND OBJECTS OF THE INVENTION

The present invention relates to a novel pump apparatus and method, the pump including a magnetically suspended and magnetically rotated impellor. The impellor impels fluid through the pump in the absence of shafts, bearings, seals, or the like. The impellor may be configured (a) for axial flow with a hollow, cylindrical-type impellor with impellor vanes on the internal surface thereof or as a streamlined body having impellor vanes located on the external surface of the body or for (b) centrifugal flow with a generally conical-like shape to the impellor which may be solid, double-ended, hollow, or the like, depending upon design considerations. One impellor design may also include a valve member secured to one end thereof to accommodate seating against a valve seat under reverse flow conditions in the event power is interrupted to the impellor. Sensors adjacent the operating position of the impellor sense the position of the impellor and provide a signal for an electronic circuit for controlling the suspension and/or position of the impellor.

It is, therefore, a primary object of this invention to provide improvements in fluid pumps.

Another object of this invention is to provide an improved method for pumping fluid with a magnetically suspended and magnetically rotated impellor.

Another object of this invention is to provide a fluid pump that is characterized by the absence of moving parts such as seals, shafts, bearings, valves, and the like.

Another object of this invention is to provide a control system for magnetically suspending an impellor inside a pump housing.

Another object of this invention is to provide a pump apparatus with a novel valve mechanism as part of the impellor to provide a valve against reverse flow in the event of power interruption to the impellor when the pump apparatus is used as a ventricular assist device.

These and other objects and features of the present invention will become more fully apparent from the following description and appended claims taken in conjunction with the accompanying drawing.

BRIEF DESCRIPTION OF THE DRAWING

FIG. 7 is a perspective view of a fourth preferred embodiment of the pump apparatus of this invention;

FIG. 8 is a cross-section taken along lines 8—8 of FIG. 7;

FIG. 9 is a partial cross-section taken along lines 9—9 of FIG. 7;

DETAILED DESCRIPTION OF THE PREFERRED EMBODIMENTS

Figure 1:
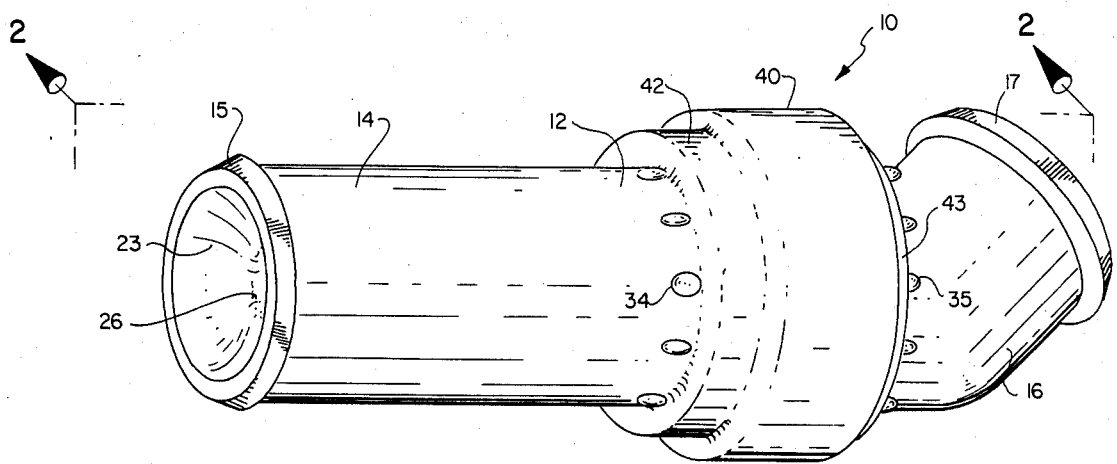
FIG. 1 is a perspective view of a first preferred embodiment of the novel pump apparatus of this invention.

The invention is best understood by reference to the drawing wherein like parts are designated with like numerals throughout.

General Discussion

The requirement for improved blood pumps is exemplified by the fact that only one total artificial heart has been implanted in a human and, further, that only moderate success has been attained by clinically applied ventricular assist devices. One of the inventors is aware of these cases and is cognizant of the limitations in the existing clinically applied devices. He is also aware of the devices currently being developed and tested in experimental laboratories. Accordingly, it is an objective of the present invention to satisfy the needs of several human engineering aspects including, for example: (1) physiological requirements, including anatomical space limitations; (2) responsive regulation; (3) safety to other systems including hematologic, cardiovascular, and pulmonary; (4) noninjurious to other organ systems by (a) crowding (pressure necrosis), (b) high, local temperature, and (c) thrombo-embolism; (5) high efficiency to minimize heating and to maximize operational time per battery density; (6) cosmetic and psychological acceptability with (7) high reliability and confidence in durability and maintenance freedom, and (8) low cost of the device.

To be suitable as a blood pump, the pump should be able to adequately meet the physiological perfusion needs of a ventricular or biventricular assist device or for total heart replacement. As a total heart replacement device, the pump should be of relatively small size and mass and be completely devoid of flexing diaphragms or surfaces as well as bearings, friction by rubbing or wearing from mechanical moving parts, etc. Additionally, the pump should be able to effectively dissipate any generated heat into the flowing blood at a sufficiently low level to preclude damage to the blood.

Figure 2:
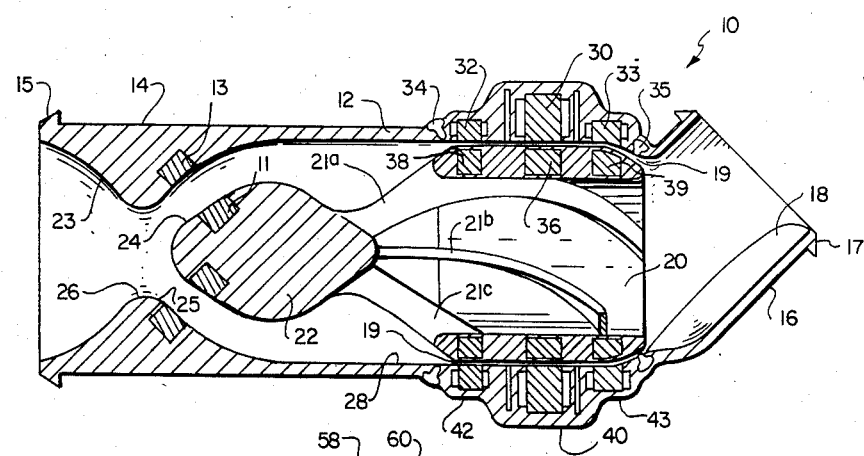
FIG. 2 is a cross-section taken along lines 2—2 of FIG. 1.

The Embodiment of FIGS. 1 and 2

Referring now more particularly to FIGS. 1 and 2, a first preferred embodiment of the pump apparatus of this invention is shown generally at 10 and includes a pump housing 12 having an inlet 14 and an outlet 16. A coupling 15 is mounted to the end of inlet 14 and serves as an attachment site for attaching pump 10 to either a natural vessel or artificial tubing (not shown). Coupling 17 provides the same features for outlet 16. Clearly, of course, coupling 15 and 17 could be of any suitable configuration to adapt pump 10 for interconnection with any desired tubing, blood vessel, or the like.

A drive housing 40 circumscribes pump housing 12 at a position corresponding with the internal location of an impellor 20 (FIG. 2), as will be set forth more fully hereinafter, and includes annular support housings 42 and 43 on each side. A plurality of sensors 34 and 35 are spaced around the periphery of pump housing 12 adjacent support housings 42 and 43, respectively. The function of each of these components will be discussed more fully hereinafter.

Referring now also to FIG. 2, a cross-sectional view of pump apparatus 10 is shown to reveal its internal structure and to more particularly set forth the internal arrangement thereof. Support housing 42 encloses an annularly arrayed set of electromagnets 32 while support housing 43 encloses a corresponding, annularly arrayed set of electromagnets 33. Electromagnets 32 are spaced from electromagnets 33 and each set is selectively controlled to provide the appropriate spatial support of impellor 20. In particular, electromagnets 32 and 33 maintain the coaxial relationship of impellor 20 inside pump chamber 28, as will be discussed more fully hereinafter.

Impellor 20 is configured as a hollow, cylindrical member having a plurality of curvilinear vanes 21a-21c mounted on its internal surface. The curvilinear nature of vanes 21a-21c is in the form of parallel, spiral vanes such that axial rotation of impellor 20 in the appropriate direction causes vanes 21a-21c to axially impel fluid through pump apparatus 10 from inlet 14 to outlet 16. Vanes 21a-21c are joined in a valve body 22. Valve body 22 has an external diameter or valve face 24 sufficient to allow it to rest against a valve seat 25 and thereby obstruct a throat 26 of an inlet valve 23. The function of valve body 22 in cooperation with inlet valve 23 will be discussed more fully hereinafter.

Impellor 20 (in combination with valve body 22) includes a plurality of internally embedded, permanent magnets, magnet sets 11, 36, 38, and 39, annularly arrayed around valve body 22 and impellor 20, respectively. Permanent magent set 36 cooperates with the corresponding electromagnet set 30 while permanent magnet set 38 cooperates with electromagnet set 32 and permanent magnet set 39 cooperates with electromagnet set 33. Operationally, the flow of electrical current to each of electromagnet sets 30, 32, and 33 is selectively regulated to control both the rotation and orientation, respectively, of impellor 20. For example, rotation of impellor 20 is controlled by pump drive circuit 120 (FIG. 5) directing the input of electrical current to electromagnet set 30. Electromagnet set 30 thus acts as the drive mechanism for rotating impellor 20 in cooperation with permanent magnet set 36.

Figure 5:
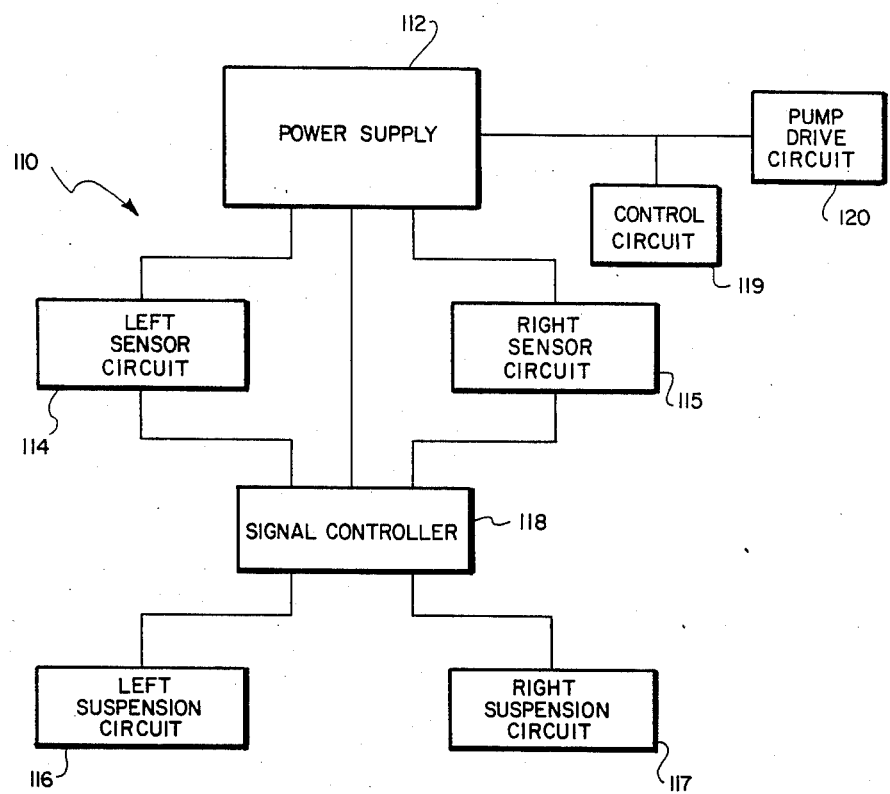
FIG. 5 is a block diagram of an electronic circuit for controlling and driving the novel pump apparatus of this invention.

Electrical energy input to each of electromagnet sets 13, 32, and 33 is selectively regulated by the appropriate suspension circuits (suspension circuits 116 and 117, FIG. 5). These electromagnet sets·cooperate with permanent magnet sets, 11, 38, and 39, respectively, to control the coaxial orientation of impellor 20 within pump housing 12. For example, a slight offset in the orientation of impellor 20 (as detected by the plurality of detectors 34 and 35) will cause sensor circuits 114 and 115 (FIG. 5) to electrically activate the appropriate sections of electromagnet sets 13, 32 and 33 to provide the necessary increase or decrease in repulsive/attractive forces to thereby selectively reorient the suspension of impellor 20 coaxially within pump housing 12.

Detector sets 34 and 35 are configured as a plurality of sensor/detector sets which emit and detect a signal as a function of the distances sensed. The sensor system may use either conventional ultrasound, infrared, or other suitable sensor systems. The system operates by detecting changes in signal intensity and/or frequency as a function of changes in the relative position of impellor 20. These signal changes are received by the appropriate sensor circuit (left sensor circuit 114 or right sensor circuit 115, FIG. 5), and interpreted by signal controller 118 (FIG. 5). Electrical energy is thereby suitably regulated to either or both of electromagnet sets 32 and/or 33 to suitably adjust and/or maintain the predetermined deposition of impellor 20 inside pumping chamber 28. Importantly, impellor 20 is suspended within the confines of pumping chamber 28 with a narrow annular space 19 surrounding the same. Annular space 19 provides clearance for impellor 20 and also, advantageously, accommodates a limited backflush of fluid therethrough to preclude stagnation, heat buildup, or the like between impellor 20 and housing 12.

Figure 4:
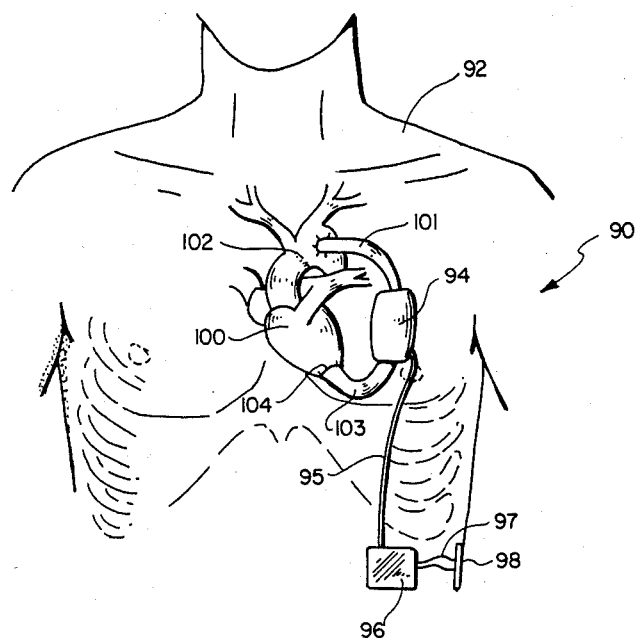
FIG. 4 is a schematic illustration of one embodiment of the pump apparatus of this invention shown in the environment of a human torso while being used as a ventricular assist device.

With particular reference also to FIG. 4, pump 10, FIGS. 1 and 2, is shown schematically at 90 as a ventricular assist pump 94 in the environment of a human torso 92. Pump 94 is interconnected at apex 104 of a heart 100 by an inlet conduit 103. An outlet conduit 101 interconnects pump 94 to the aortic arch 102. Accordingly, the natural heart 100 is not replaced but is merely assisted with pump 94, either as a long-term implant or as a temporary assist device. In the embodiment shown, pump 94 is implanted as a semipermanent implantation and includes a power supply 96 supplying power to pump 94 through leads 95. Leads 97 connect power supply 96 to an induction coil 98 so that power supply 96 can be recharged by bringing a corresponding induction coil (not shown) adjacent induction coil 98 according to conventional techniques.

Pump 10 (FIGS. 1 and 2) and pump 94 (FIG. 4) are both adapted as ventricular assist devices. Pump 10 is particularly adapted since it includes the valve mechanism of valve seat 25 adapted to receive valve face 24 of valve body 22. As a ventricular assist device, pump 10 is used only to supplement the pumping action of heart 100 (FIG. 4) so that an interruption of electrical power to electromagnets 13, 30, 32, and 33 will not be catastrophic. Instead, the existing backpressure in pump 10 causes a momentary reverse flow of fluid from outlet 16 toward inlet 14 with a corresponding reverse movement of impellor 20 toward inlet 14. This reverse movement brings valve body 22 and, more particularly, valve face 24 into sealing contact with valve seat 25. In this manner, reverse flow is promptly stopped upon failure of pump 10.

Referring again to FIG. 2, outlet 16 is shown having an angular offset from the axial orientation of pump housing 12 for the purpose of (1) more readily adapting pump apparatus 10 to placement within the anatomical space adjacent a heart and (2) decreasing the tendency for the pumped blood to swirl as a result of being pumped by rotation of impellor 20. Swirling motion is also decreased by including a stator vane 18 inside outlet 16.

Figure 3:
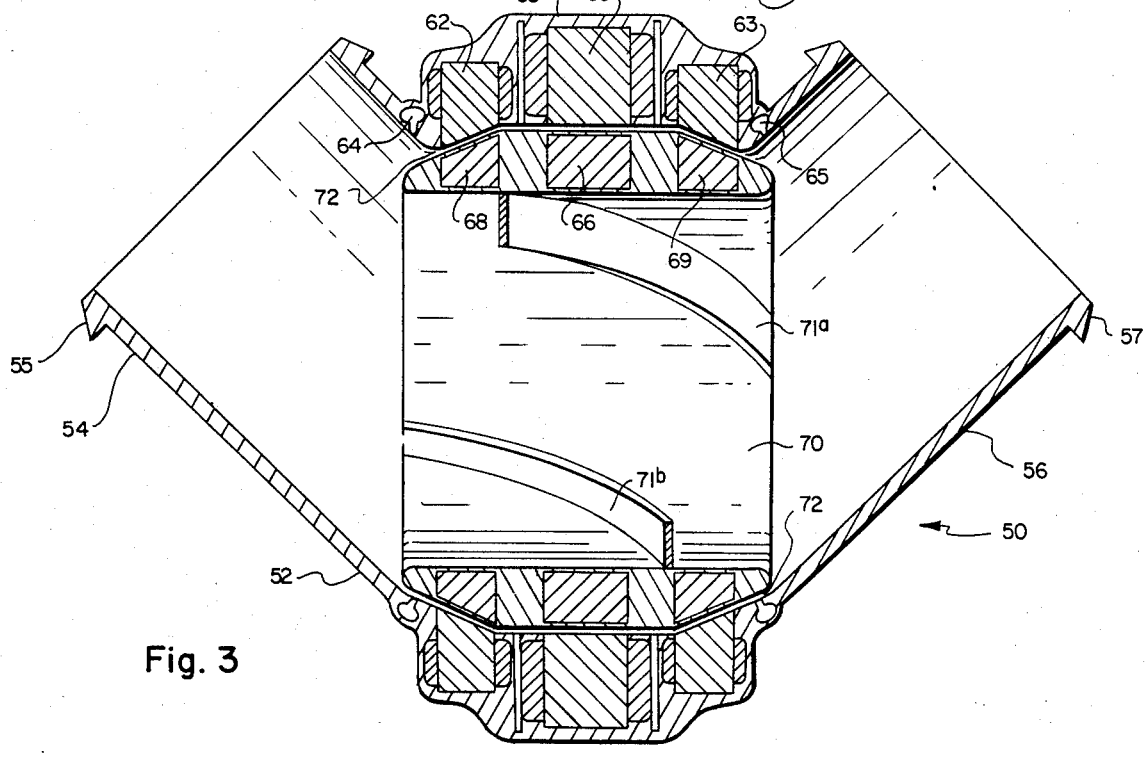
FIG. 3 is a cross-sectional view of a second preferred embodiment of the novel pump apparatus of this invention.

The Embodiment of FIG. 3

Referring now more particularly to FIG. 3, a second preferred embodiment of the novel pump apparatus of this invention is shown generally at 50 and includes a pump housing 52 having an inlet 54 and an outlet 56. An attachment site 55 is provided on inlet 54 and an attachment site 57 is provided on outlet 56 for the purpose of readily adapting pump apparatus 50 to be interconnected into the appropriate size natural and/or artificial tubing (not shown, but see conduits 103 and 101, respectively, FIG. 4). Although pump apparatus 50 is shown substantially enlarged over that of pump apparatus 10 (FIGS. 1 and 2), it should be clearly understood that the size may be selectively predetermined and is shown enlarged herein only for ease of illustration convenience.

Pump 50 includes a drive and support housing 58 enclosing an inlet electromagnet support set 62, an outlet support electromagent set 63 and a drive electromagnet set 60 therein. An impellor 70 within pump housing 52 is configured as a hollow cylindrical member having a plurality of impellor vanes 71a and 71b mounted on the interior surface thereof. A plurality of permanent magnet sets 66, 68, and 69 are embedded in the external periphery of impellor 70. Permanent magnet set 68 corresponds to inlet support electromagnet set 62 and permanent magnet set 69 corresponds to outlet electromagnet support set 63 while permanent magnet set 66 corresponds to drive electromagnet set 60. Accordingly, the overall function of impellor 70 is substantially similar to the operation of impellor 20 (FIG. 2), as set forth hereinbefore. Axial rotation of impellor 70 causes impellor vanes 71a and 71b to push against the fluid (not shown) impelling the same from inlet 54 toward outlet 56.

It should be noted that the angular orientation between inlet 54 and outlet 56 relative to impellor 70 is such that it more readily adapts pump apparatus 50 to placement in the anatomical cavity adjacent or in place of the natural heart while substantially reducing the swirling action imparted to the fluid by impellor 70, as set forth hereinbefore with respect to pump apparatus 10 (FIGS. 1 and 2). Pump 50 may also include guide vanes 18 (FIG. 2) to reduce swirl in the pumped fluid. From the foregoing, it is clear that pump apparatus 50 is substantially similar in operation to pump apparatus 10 with the exception that pump apparatus 50 does not include a valve member 22 affixed thereto.

Pump apparatus 50 includes a plurality of inlet sensors 64 and outlet sensors 65 to selectively determine the orientation of impellor 70 relative to pump housing 52. The position of impellor 70, as detected by sensors 64 and 65, is selectively controlled by a signal controller 118 (FIG. 5) which in turn selectively controls each of electromagnet sets 62 and 63. Importantly, the spatial orientation of impellor 70 is maintained coaxially within housing 52 with a surrounding space 72 which permits backflush and also precludes rubbing by impellor 70.

Figure 6:
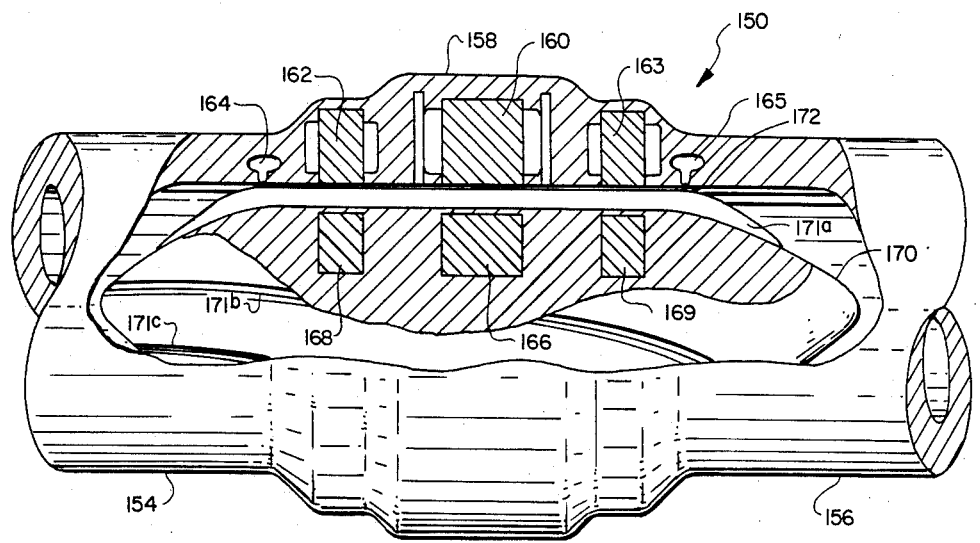
FIG. 6 is a frontal elevation of a third preferred embodiment of the pump apparatus of this invention with portions broken away to reveal internal structure thereof.

The Embodiment of FIG. 6

Referring now more particularly to FIG. 6, a third preferred embodiment of the pump apparatus of this invention is shown generally at 150 and includes a pump housing 158 having an inlet 154 and an outlet 156 with an impellor 170 suspended therein. Pump housing 158 encloses a plurality of electromagnet sets 160, 162 and 163. Electromagnet set 160 forms an annular array and serves as a drive electromagnet system for axially rotating impellor 170. Electromagnet sets 162 and 163 form annular arrays of electromagnets at each end of impellor 170 and are selectively controlled to provide the necessary suspension or orientation of impellor 170 inside pump housing 158. The position of impellor 170 is determined by detector sets 164 and 165 annularly arrayed around pump housing 158. A controller such as signal controller 118 (FIG. 5) electronically analyzes signals received by the plurality of detectors 164 and 165 and provides the necessary control signals to the left and right suspension circuits (left suspension circuit 116 and right suspension circuit 117, FIG. 5) for driving electromagnet sets 162 and 163.

Impellor 170 is configured as a cylindrical, aerodynamic body and includes a plurality of impellor vanes 171a-171c mounted externally thereon. Impellor 170 also includes a plurality of annularly arrayed permanent magnet sets 166, 168, and 169 corresponding generally to magnet sets within the various impellors, impellor 70, (FIG. 3) and impellor 20 (FIG. 2). Electromagnet sets 162 and 163 cooperate with permanent magnet sets 168 and 169, respectively. Impellor 70 is suspended inside the pump housing of pump 150 with a space 172 maintained therebetween to minimize rubbing by impellor 170. Drive electromagnet set 160 cooperates with permanent magnet set 166 for the purpose of causing rotation of impellor 170.

The primary difference between the pump apparatus 150 of this third preferred embodiment and that of either of the second or third preferred embodiments of FIGS. 1-3 is that the impellor vanes, impellor vanes 171a-171c, are mounted on the external surface of impellor 170, whereas the various impellor vanes of the other two embodiments are located on the internal surface of a hollow, cylindrical impellor member. Impellor 170 could also include a valve member similar to valve member 22 (FIG. 2) formed on the inlet end adjacent inlet 154 to cooperate with a valve seat (not shown) configured substantially similar to valve seat 25 (FIG. 2).

Referring now more particularly to FIG. 5, the electronic circuitry of the control, sensor, and suspension circuits are conventional systems and are, therefore, shown schematically. These systems include a power supply 112 electrically connected to the pump drive circuit 120 controlled by control circuit 119. A left sensor circuit 114 and a right sensor circuit 115 provide the necessary signal input to a signal controller 118 which, in turn, provides the necessary control signals to left suspension circuit 116 and right suspension circuit 117, respectively, to thereby selectively control the orientation and suspension of the respective impellor inside of the respective pump housing. Additionally, the appropriate feedback circuitry is provided to accommodate sensing the electromotive force being applied to the pump drive circuit as a function of pressure to thereby readily adapte the apparatus and method of this invention for being able to regulate pressure as determined by the pump drive circuit and the amount of energy input to the respective drive electromagnet set.

The Embodiment of FIGS. 7-9

Referring now more particularly to FIGS. 7-9, a fourth preferred embodiment of the novel pump apparatus of this invention is shown generally at 200 and includes a pump housing 202 with an impellor 220 suspended and rotated magnetically therein as will be discussed more fully hereinafter. Inlets 204 and 206 are provided on opposing faces of pump housing 202 for receiving fluid therein. Each of inlets 204 and 206 have rims 205 and 207, respectively, formed thereon for ease in attaching tubing (not shown) to pump 200. The dual inlets 204 and 206 are believed to provide a more uniform flow pattern for pump 200 thereby substantially minimizing the balance requirements for impellor 220 with a corresponding lower consumption of energy for the magnetic bearing system. Impellor 220 is configurated with a conical apex 210 and 212 on each end thereof to present a smooth flow profile to the incoming fluid through the respective inlets 204 and 206. Fluid (not shown) drawn into pump 200 through inlets 204 and 206 is centrifugally impelled outwardly through a discharge conduit 208 formed as a tangential outlet. A rim 209 on conduit 208 serves as an attachment site for tubing (not shown) to pump 200. Incoming fluid through inlet 204 is received in an inlet chamber 214 while incoming fluid through inlet 206 is received in an inlet chamber 216. Rotation of impellor 220 causes impellor vanes 250 and 251 to impart an outward centrifugal momentum to the fluid forcing it into two peripheral, scroll chambers 228 and 230 and join as discharge conduit 208. A septum 224 divides scroll chamber 230 into an outer scroll chamber 226 and an inner scroll chamber 228 (FIG. 9) for reduction of turbulence during operation of pump 200. Septum 224 not only reduces tubulence, but also lowers any tendency toward cavitation, stagnation, and the like, that would otherwise be experienced by fluid in scroll chamber 230. The structure of septum 224 provides two tangential outlets 180 apart to compensate for the radial forces on impellor 220 with a corresponding lower consumption of energy for the magnetic bearing system.

A permanent magnet 264 is configured as a cylindrical magnet extending between conical apexes 210 and 212. Permanent magnet 264 cooperates between ring magnets 236 and 238 to which are coupled coil windings 237 and 239, respectively, to assist in maintaining the directional stability of pump impellor 220. A plurality of C-shaped electromagnets 232-235 (FIG. 9) cooperate with corresponding permanent magnets 260-263 in the circumferential periphery of impellor 220 to cause the same to rotate in a generally clockwise direction (when viewed in FIG. 9). Windings 232a and 232b with respect to electromagnet 232 and windings 234a and 234b with respect to electromagnet 234 control the repulsive/attractive forces of the respective magnet systems. Pump 200 also includes a sensor system (see FIGS. 1-3, 5 and 6) whereby the orientation of impellor 220 is magnetically suspended within pump housing 202 so that the desired spatial separation or gap 222 is maintained between impellor 220 and pump housing 202. Clockwse rotation of impellor 220 causes vane sets 250 and 251 thereon to impart the necessary propulsion to the fluid entering inlets 204 and 206, respectively, and impel the same through scroll chamber 230.

Figure 10:
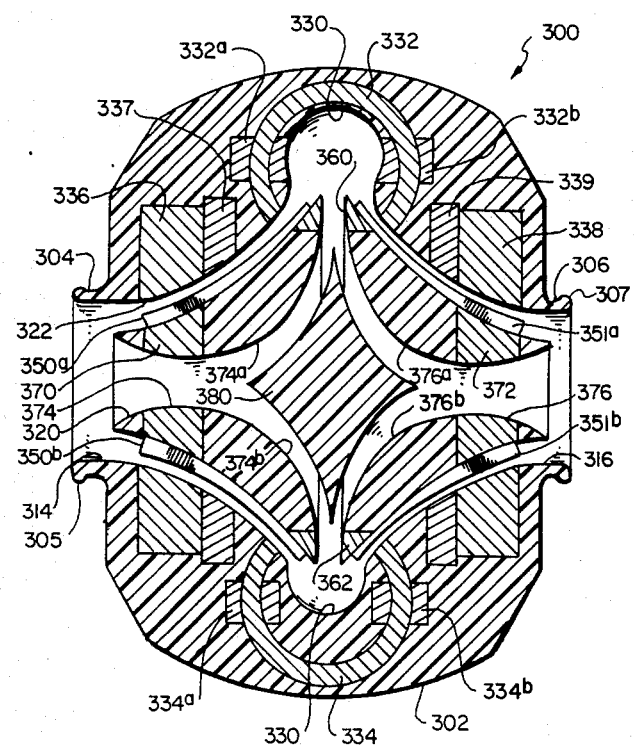
FIG. 10 is a cross-section of a fifth preferred embodiment of the novel pump apparatus of this invention.

The Embodiment of FIG. 10

Referring now more particularly to FIG. 10, an axial, cross-sectional view of a fifth preferred embodiment of the novel pump apparatus of this invention is shown generally at 300 and includes a pump body 302 havng an impellor 320 magnetically suspended and rotated therein as will be discussed more fully hereinafter. Dual inlets to pump 300 are provided by inlets 304 and 306 with fluid being drawn thereinto into inlet chambers 314 and 316, respectively.

Impellor 320 impels the fluid into a surrounding scroll chamber 330 during the pumping operation. Impellor 320 is configurated as a generally hollow impellor having inlet ports 374 and 376 splitting into discharge channels 374a and 374b and discharge channels 376a and 376b, respectively. A flow profile body 380 is supported interiorily inside impellor 320 by supports (not shown). Flow profile body 380 is configured with a generally double conical configuration to provide a smooth flow profile through the hollow interior of impellor 320. The external surface of impellor 320 includes a plurality of vanes 350a and 350b on the side of inlet 304 and vanes 351a and 351b on the side of inlet 306. The combination of vanes 350a, 350b, 351a, and 351b, in combination with the hollow center to impellor 320 provides a substantially improved flow pattern for impellor 320.

Permanent magnets 370 and 372 embedded in each end of impellor 320 respectively cooperate with electromagnet sets 336 on the left and electromagnet set 338 on the right, each of the respective electromagnet sets being selectively controlled by windings 337 and 339, respectively. This combination of permanent magnets and corresponding electromagnet sets provides the necessary suspension system for impellor 320 in pump body 302. Suspension of impellor 320 is achieved by a sensor and suspension system (not shown, but see FIGS. 1-3, 5, and 6) so that impellor 320 is magnetically suspended in housing 302 to provide the desired spatial separation or gap 322 between impellor 320 and housing 302.

A plurality of permanent magnets 360 and 362 are embedded in the circumferential periphery of impellor 320 and cooperate with horseshoe-shaped electromagnets 332 and 334. Electromagnets 332 and 334 are selectively driven by windings 332a and 332b with respect to electromagnet 332 and windings 334a and 334b which drive electromagnet 334. Electromagnets 332 and 334 cooperate with permanent magnets 360 and 362 to drive impellor 320 in the appropriate direction for the pumping operation.

Figure 11:
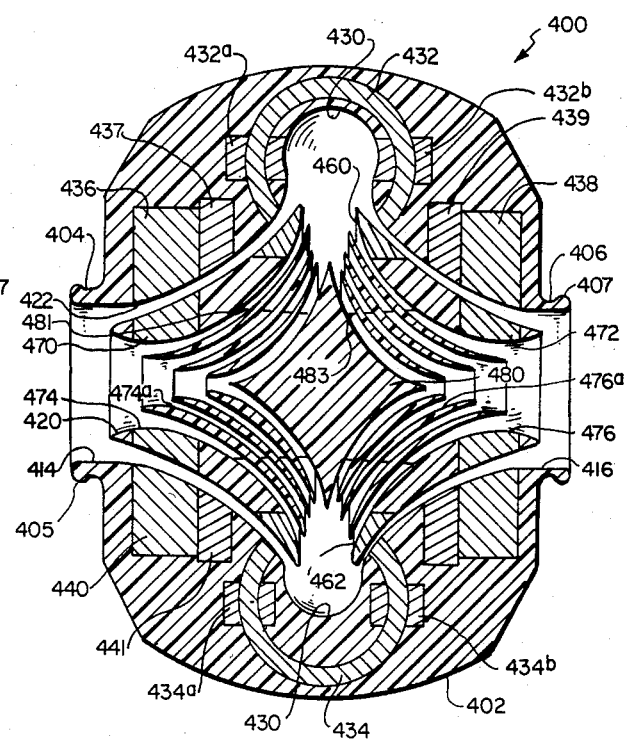
FIG. 11 is a cross-sectional view of a sixth preferred embodiment of the novel pump apparatus of this invention.

The Embodiment of FIG. 11

Referring now more particularly to FIG. 11, a sixth preferred embodiment of the novel pump apparatus of this invention is shown generally at 400 and includes a pump housing 402 with an impellor 420 magnetically suspended and rotated therein. Inlets 404 and 406 on each end of pump housing 402 admit fluid into inlet chambers 414 and 416, respectively. Rims 405 and 407 on inlets 404 and 406, respectively, provide attachment sites for natural or artificial tubing (not shown) to pump 400. Fluid entering inlet chambers 414 and 416 is centrifugally impelled by impellor 420 into a surrounding scroll chamber 430.

Impellor 420 is configured as a generally hollow impellor having an inlet 474 and a plurality of guide vanes 474a therein on one side and a corresponding hollow inlet 476 with a plurality of guide vanes 476a therein on the other side. The central position of impellor 420 is occupied by a flow profile body 480 configurated as a double apex cone member to present a smooth flow profile for fluid passing through the hollow center of impellor 420. Guide vanes 474a and 476a are supported interiorily in impellor 420 by support members indicated schematically herein as support members 481 and 483. Rotation of impellor 420 causes fluid entering inlet chambers 414 and 416 to be drawn through the passageways between guide vanes 474a and 476a, respectively, and through the surrounding gap 422 between impellor 420 and pump housing 402 centrifugally discharging the same into the surrounding scroll chamber 430.

A permanent magnet 470 embedded in one end of impellor 420 cooperates with surrounding electromagnet set 436 controlled by windings 437 to suitably suspend the left side of impellor 420 in the hollow of pump housing 402. Correspondingly, a permanent magnet 472 cooperates with a surrounding electromagnet set 438 controlled by windings 439 to suspend the right side of impellor 420 in pump housing 402. A suitable sensor/suspension system (see FIGS. 1-3, 5 and 6) is provided to maintain the spatial orientation of impellor 420 inside pump housing 402.

Rotation of impellor 420 is provided by a plurality of permanent magnets 460 and 462 embedded in the circumferential periphery of impellor 420. Permanent magnets 460 and 462 cooperate with C-shaped electromagnets 432 and 434 (as controlled by windings 432a and 432b with respect to electromagnet 432 and windings 434a and 434b with respect to electromagnet 434) to impart the necessary rotational movement of impellor 420. Electrical energy to drive the respective windings of electromagnets 432 and 434 is supplied by a pump drive circuit 120 (FIG. 5). It will be noted that impellor 420 does not incorporate vanes (for example, see vane sets 350 and 351, FIG. 10). Instead, impellor 420 relies on the natural frictional engagement between the extended surface areas interiorily and exteriorily of impellor 420 in cooperation with the relatively narrow spatial separation of these surfaces to cause impellor 420 to centrifugally impel the fluid into scroll chamber 430.

Figure 12:
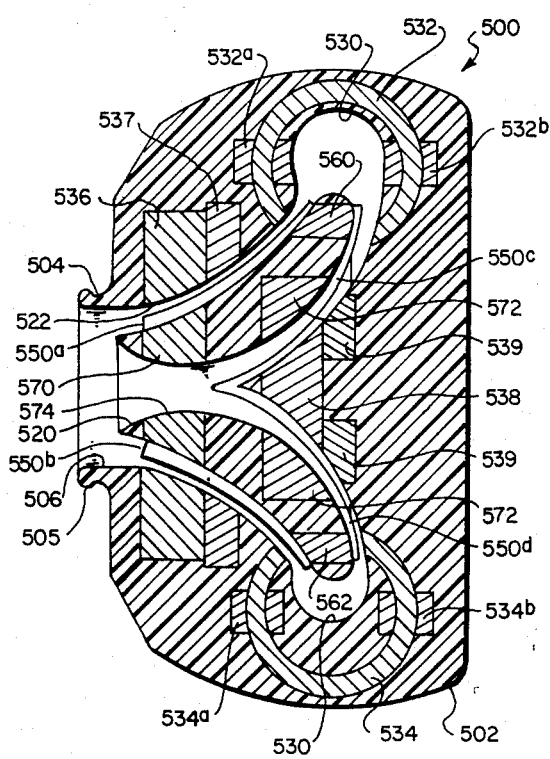
FIG. 12 is a cross-sectional view of a seventh preferred embodiment of the novel pump apparatus of this invention.

The Embodiment of FIG. 12

Referring now more particularly to FIG. 12, a seventh preferred embodiment of the novel pump apparatus of this invention is shown generally at 500 and includes a pump housing 502 with an impellor 520 magnetically suspended and rotated therein between an inlet 504 and a surrounding scroll chamber 530. A rim 505 on inlet 504 serves as an attachment site for the attachment of a tubing (not shown) to inlet 504. It will be particularly noted with respect to pump 500 that only a single inlet 504 having an inlet chamber 506 is provided. Rotation of impellor 520 causes incoming fluid to be discharged into scroll chamber 530.

Impellor 520 includes a hollow center 574 having vanes 550c and 550d on the inner surface thereof while vanes 550a and 550b are mounted exteriorly of impellor 520. Incoming fluid into an inlet chamber 506 either passes exteriorly of impellor 520, as impelled by vanes 550a and 550b, or otherwise interiorily of impellor 520 as impelled by impellor vanes 550c and 550d with the impelled fluid being discharged into the surrounding scroll chamber 530. Impellor 520 is suspended in pump body 502 by cooperation between permanent magnets 570 and 572, embedded in impellor 520 and corresponding electromagnet set 536 controlled by windings 537 in addition to electromagnet 538 and controlled by winding 539 to magnetically suspend impellor 520 in the pump body 502. A sensor/suspension system (for example, see FIGS. 1-3, 5, and 6) is provided to selectively control windings 537 and 539 to thereby maintain the desired orientation of impellor 520 inside pump housing 502 and, more particularly, the spatial separation or gap 522 between impellor 520 and pump housing 502.

Permanent magnets 560 and 562 are mounted on the periphery of impellor 520 and cooperate with C-shaped electromagnet 532 (controlled by windings 532a and 532b) and electromagnet 534 (controlled by windings 534a and 534b) to impart the necessary rotary motion to impellor 520. A pump drive circuit (pump drive circuit 120, FIG. 5) selectively provides the necessary electrical energy to windings 532a, 532b, 534a and 534b to cause impellor 520 to be rotated inside pump housing 502.

Figure 13:
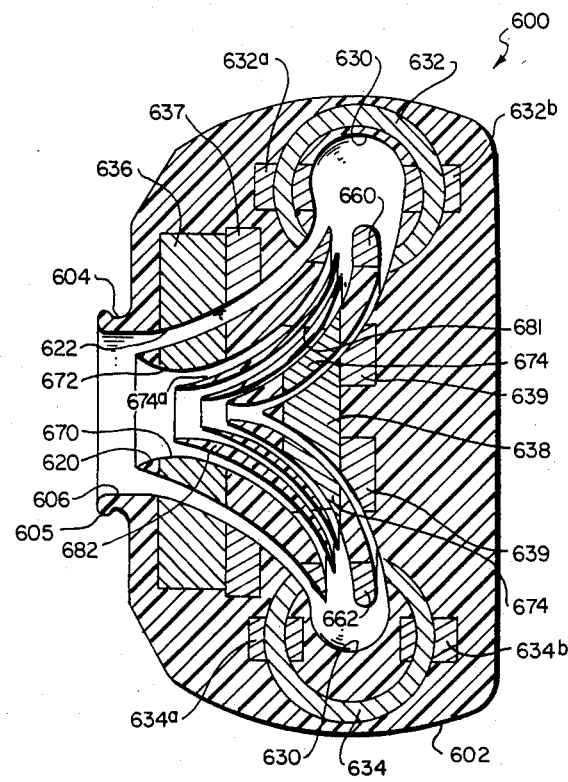
FIG. 13 is a cross-sectional view of an eighth preferred embodiment of the novel pump apparatus of this invention.

The Embodiment of FIG. 13

Referring now more particularly to FIG. 13, an eighth preferred embodiment of the novel pump apparatus of this invention is shown generally at 600 and includes a pump housing 602 having an impellor 620 magnetically suspended and rotated therein. A single inlet 604 admits a fluid into an inlet chamber 606. A rim 605 on inlet 604 serves as an attachment site for tubing (not shown) mounted to pump 600.

Impellor 620 is configurated substantially similar to impellor 520 (FIG. 12) with the exception that impellor 620 includes a plurality of guide vanes 682 mounted interiorily on spaced mounting brackets indicated generally at 681. The interior of impellor 620 provides a flow channel 674 divided into a plurality of subflow channels 674a by guide vanes 682 thereby substantially eliminating undue turbulence, backflow, and the like that might otherwise be experienced upon rotation of impellor 620.

Impellor 620 is suspended in pump housing 602 by a plurality of permanent magnets 672 and 674 embedded therein and which cooperate with a corresponding electromagnetic support system. The electromagnetic support system is provided by electromagnet set 636 (controlled by winding 637) and electromagnet 638 (controlled by winding 639) which cooperate with permanent magnets 672 and 674, respectively, to suspend impellor 620 inside pump housing 602. A sensor/suspension circuit (for example, see FIGS. 1-3, 5 and 6) is provided to selectively suspend impellor 620 inside pump housing 602 with the appropriate spatial separation or gap 622 therebetween.

Impellor 620 also includes permanent magnets 660 and 662 embedded in the external periphery. Permanent magnets 660 and 662 cooperate sequentially with C-shaped electromagnet 632 (controlled by windings 632a and 632b) in combination with C-shaped electromagnet 634 (controlled by windings 634a and 634b), respectively. A pump drive circuit (pump drive circuit 120, FIG. 5) selectively provides the necessary electrical energy to windings 632a, 632b, 634a and 634b to cause impellor 620 to be rotated inside pump housing 602.

In each of the embodiments set forth herein in FIGS. 7-13, it will be noted that the pump apparatus is configurated as a centrifugal pump apparatus wherein a coaxial inflow of fluid is impelled outwardly by a rotating impellor into the surrounding scroll chamber and discharged tangentially through the corresponding outlet, such as outlet 208 (FIGS. 7 and 9). The pumping apparatus of FIGS. 7-11 discloses double inlets at each end of the impellor, with the impellor therein being configurated as a generally double-ended conical member. Dual inlets advantageously balance the axial forces against the respective impellor as the fluid is impelled outwardly by the impellor. This balancing of forces substantially reduces the energy consumption of the magnetic suspension system. The pump apparatus of FIGS. 10 and 11 disclose variations in hollow impellor apparatus for improved flow profiles therethrough.

The pump apparatus of FIGS. 12 and 13 relates to a single inlet pump with variations in the flow profile through the center of the impellor suspended therein. The impellors of FIGS. 12 and 13 are configured with a flow-through channel to preclude stagnation of fluids behind the impellor as would otherwise occur if there were no flow channel.

Importantly, each impellor can be fabricated from suitable materials so that the specific gravity of the impellor can be made to match the specific gravity of the particular fluid being pumped. This matching of specific gravities is particularly desirable in that it reduces the energy required to magnetically suspend the impellor during operation and also the energy required to magnetically overcome external acceleration forces upon sudden movements of the entire pump. The selection of materials of construction is also directed toward the unencumbered selection of blood-compatible materials, many of which are well-known in the art.

In each embodiment herein, the design of each impellor is specifically coordinated to minimzie hemolysis of the blood due to critical shear stresses imposed on the blood, particularly in the gap between the moving impellor and the stationary housing. Clearly, the size of the required gap is a function of the radial velocity of the impellor as determined by the diameter of the impellor and the rate of rotation. For most blood pump operations, this gap is about 1 mm.

The driving system for rotating the respective impellors can be of any suitable type such as an asynchronous motor, especially one using induced eddy currents. Also, it is to be clearly understood that the driving systems and the magnetic suspension systems can be configured to use the same components simultaneously. Rotational speed can be controlled by a closed loop system using either the signal of the position sensors of the magnetic suspension system or the induced electromotive forces. Sensors similar to sensor sets 34 and 35 (FIGS. 1 and 2), sensor sets 64 and 65 (FIG. 3), or sensor sets 164 or 165 (FIG. 6) may be included selectively in any of pump 200 (FIGS. 7-9), pump 300 (FIG. 110), pump 400 (FIG. 11), pump 500 (FIG. 12), and pump 600 (FIG. 13).

Further details of preferred embodiments of blood pump having a magnetically suspended rotor or impellor, invented by two of the inventors of the blood pumps disclosed herein, are disclosed in the co-pending patent application entitled "Magnetically Suspended and Rotated Rotor", U.S. Ser. No. 720,081, filed on Apr. 4, 1985, which hereby specifically is incorporated herein by reference.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A blood pump comprising:
   a pump housing;
   a pump rotor disposed in the housing and including a rotor shaft having opposite ends;
   magnetic rotation means for magnetically rotating the rotor; and
   magnetic suspension means for magnetically suspending the rotor in the housing, comprising:
      permanent magnet means located in the rotor shaft, one portion of the permanent magnetic means being located near one end portion of the rotor shaft and another portion of the permanent magnet means being located near the opposite end portion of the rotor shaft;
      permanent magnet means located at two axially spaced locations in the pump housing, one being positioned to cooperate with one of the permanent magnet means located at the one end portion of the rotor shaft and the other being positioned to cooperate with the other permanent magnet means located at the opposite end portion of the rotor shaft;
      electromagnet means in the pump housing located at two axially spaced locations in the pump housing, one being positioned to cooperate with the portion of the permanent magnet means located at the one end portion of the rotor shaft and the other being positioned to cooperate with the the portion of the permanent magnet means located at the opposite end portion of the rotor shaft;
      a sensor for sensing the position of the pump rotor in the pump housing and providing a sensor signal indicative of the position of the pump rotor in the pump housing; and
      a controller electrically connected between the sensor and the electromagnet means in the pump housing for supplying the control signal to the electromagnet means in response to the sensor signal for adjusting the position of the pump rotor in the pump housing as a function of the control signal.

2. The blood pump of claim 1 wherein the pump housing is characterized as having two inlets positioned at opposite ends of the pump rotor and an outlet positioned adjacent the outer periphery of central portions of the pump rotor.

3. The blood pump of claim 1 wherein the pump rotor is characterized as having a specific gravity substantially equal to the specific gravity of blood.

* * * * *